United States Patent [19]

Camaioni et al.

[11] Patent Number: 5,708,246

[45] Date of Patent: Jan. 13, 1998

[54] METHOD OF PHOTOCATALYTIC CONVERSION OF C-H ORGANICS

[75] Inventors: Donald M. Camaioni; Michael A. Lilga, both of Richland, Wash.

[73] Assignee: Battelle Memorial Institute, Richland, Wash.

[21] Appl. No.: 705,473

[22] Filed: Aug. 28, 1996

[51] Int. Cl.⁶ .................. C07F 1/00; C07F 3/00; C07C 51/00; C07C 67/00
[52] U.S. Cl. .................. 204/157.6; 204/157.63; 204/157.87
[58] Field of Search .................. 204/157.6, 157.63, 204/157.87, 157.9, 157.92; 205/440, 441, 452

[56] References Cited

U.S. PATENT DOCUMENTS

| | | | |
|---|---|---|---|
| 3,067,115 | 1/1962 | Clingman, Jr. | 204/157.63 |
| 3,917,708 | 11/1975 | Kuessner et al. | 260/586 |
| 4,434,031 | 2/1984 | Horowitz et al. | 205/440 |
| 4,571,290 | 2/1986 | Ward et al. | 204/157.9 |
| 5,233,113 | 8/1993 | Periana et al. | 585/500 |
| 5,306,855 | 4/1994 | Periana et al. | 585/500 |
| 5,364,508 | 11/1994 | Weres et al. | 204/128 |

FOREIGN PATENT DOCUMENTS 1026971 2/1966 United Kingdom .

OTHER PUBLICATIONS

Harima et al., "Anodic Processes on n-TiO2 with and without illumination in Trifluoromethanesulfonic Acid Monohydrate Saturated with Alkanes", J. Phys. Chem., vol. 92, pp. 5716-5721, 1988.

Anodic Processes on n-$TiO_2$ With and Without Illumination in Trifluoro–Methanesulfonic Acid Monohydrate Saturated With Alkanes, Harima et al., J. Phys. Chem., 1988, 92, 5716–5721, month unavailable.

Selective Intermolecular Carbon–Hydrogen Bond Activation by Synthetic Metal Complexes in Homogeneous Solution, Arndtsen et al., Acc. Chem. Res. 1995, 28, 154–162, month unavailable.

Products and Mechanism of the Oxidation of 9–Methylanthracene by Peroxydisulfate, Proton Loss and Nucleophile Addition Reactions of the 9–Methylanthracene Radical Cation, Dearduff et al., Journal of Organic Chemistry, 1986, 51, 3686, month unavailable.

Novel Approach Taken for Methane Activation, J. Haggin, Jan. 18, 1988, C&EN.

Carbon–Hydrogen Bond Activation by Electrophilic Transition–Metal Compounds. Palladium(II)–Mediated Oxidation of Arenes and Alkanes Including Methane, Gretz et al, J. Am. Chem. Soc., 1987, 109,8109–8111, month unavailable.

Aerial Oxidation of Benzene in the Presence of Electrochemically Generated Cuprous Ions, Kinoshita et al, Agnew. Chem. Suppl., 1983, 599–608, month unavailable.

Carbon–Hydrogen vs. Carbon–Carbon Bond Cleavage of 1,2–Diarylethane Radical Cations in Acetonitrile–Water, DM Camaioni and JA Franz, May 2, 1983, American Chemical Society, 1984, J. Org. Chem., vol. 49, No. 9, pp. 1608–1613, month unavailable.

*Primary Examiner*—Kathryn L. Gorgos
*Assistant Examiner*—Edna Wong
*Attorney, Agent, or Firm*—Paul W. Zimmerman

[57] ABSTRACT

The present invention is the addition of a semiconductor material and energy to the reaction mixture of organic, acid (for example, trifluoroacetate), and oxygen. A transition metal ion may be added to the reaction mixture. The semiconductor material converts energy to oxidants thereby promoting oxidation of the organic. Alternatively, using metal in combination with exposure to light may be used.

22 Claims, No Drawings

1

METHOD OF PHOTOCATALYTIC CONVERSION OF C-H ORGANICS

This invention was made with Government support under Contract DE-AC06-76RLO 1830 awarded by the U.S. Department of Energy. The Government has certain rights in the invention.

FIELD OF THE INVENTION

The present invention relates generally to a photocatalytic assisted conversion of C—H compounds to C—O compounds and conversion to C—O and C—C, C=C, and C≡C compounds. The terms "C—H compound(s)" and "C—H organic compound(s)" are herein defined as any organic compound(s) having at least one carbon to hydrogen bond. The term "conversion" herein refers to processes wherein the C—H bond is replaced by a C—O bond (oxidation) or the C—H bond is replaced by a C—C, C=C, or C≡C bond. The oxidation selectively forms a single bond between the carbon and the oxygen. The term "C—O" or "C—O bond" specifically refers to a single bond between a carbon atom and an oxygen atom, and specifically excludes a double bond or triple bond between a carbon atom and an oxygen atom. The photocatalyst is a semiconductor. The term "metal" is inclusive of metal in any valence state.

BACKGROUND OF THE INVENTION

Production of alcohols and/or olefins by oxidation of organic compounds is difficult because the oxidation reaction tends toward completion to carbon dioxide. Overoxidation has been a persistent problem and arresting the oxidation at a desired intermediate oxidation product is a goal of much research.

For example in the paper, E. Gretz et al., CARBON-HYDROGEN BOND ACTIVATION BY ELECTROPHILLIC TRANSITION-METAL COMPOUNDS, PALLADIUM(II)-MEDIATED OXIDATION OF ARENES AND ALKANES INCLUDING METHANE, J. Am. Chem. Soc. 1987, 109, 8109–8111, methane and trifluoroacetate undergo selective oxidation with a palladium catalyst to obtain methyltrifluoroacetate. However, use of a noble metal is necessary and costly.

In the paper, T. Kinoshita et al., AERIAL OXIDATION OF BENZENE IN THE PRESENCE OF ELECTRO-CHEMICALLY GENERATED CUPROUS IONS, Angew. Chem. Suppl. 1983, 599–608, benzene is combined with sulfuric acid and acetonitrile together with oxygen and cupric ions, cuprous ions formed by electrochemical reduction of cupric ions, to obtain phenol, hydroquinone, and catechol. Kinoshita et al. require regeneration of the cuprous ions and the oxidation is not specific.

In the published Patent Cooperation Treaty application, publication number WO 92/17425, DM Camaioni, MA Lilga, a hydrocarbon is combined with an acid (trifluoroacetic) together with oxygen and a transition metal ion to selectively obtain an ester. Research with the metal-catalyzed free radical oxidations demonstrated that an attacking oxidizing species is generated by reducing oxygen with Cu(I) in a solution of Cu(II) and trifluoroacetic acid. The trifluoroacetate group, being more electron-withdrawing than hydroxyl, renders methyl trifluoroacetate less reactive than methanol. A disadvantage is the need for either regeneration of the metal ion(s) or replenishment of them.

In the paper, Y. Harima and S. Morrison, ANODIC PROCESSES ON n-TiO$_2$ WITH AND WITHOUT ILLU-MINATION IN TRIFLUOROMETHANESULFONIC ACID MONOHYDRATE SATURATED WITH ALKANES, J. Phys. Chem. 1988, 92, 5716–5721, a saturated hydrocarbon (propane) was combined with trifluoromethane-sulfonic acid as a mixture together with an n-TiO$_2$ electrode followed by exposure to light from a 100 W, high pressure Hg lamp. The n-TiO$_2$ was in the form of a disk serving as an anode of an electrochemical cell. The product was a polymer that collected on the surface of the n-TiO$_2$. No transition metal ion was present and no ester product was reported.

It is hypothesized that radical-based oxidations could be made selective for alcohols provided that the attacking radical is electrophilic and the product alkyl radical becomes functionalized with an electron-withdrawing group, such that the alpha C—H bond is less electron-rich compared with the parent alkane C—H. A separate subsequent chemical process converts the functionalized alkane to an alcohol. Analogous two-step approaches, using non-radical processes and metal catalysts other than Cu, have been described. While oxy radicals, such as hydroxyl and sulfate radical anion, and metal-oxo radicals, i.e., $L_nFe^{iv}O\bullet$, are capable of attacking unactivated C—H bonds, converting alkyl radicals to products that are less reactive than the alcohol is a key requirement for such radical-based systems to succeed. Rate data (see Table 1) for hydroxyl radical and sulfate radical ion show that rates of attack on Me-X compounds are dependent on the electron-withdrawing/donating properties of the X group.

TABLE 1

| Bimolecular Rate Constants for Oxy-Radical Attack on Substituted Methanes | | |
|---|---|---|
| X—CH$_3$ | HO• k/H × 10$^{-9}$M$^{-1}$s$^{-1}$ | SO$_4^{-\bullet}$ k/H × 10$^{-6}$M$^{-1}$s$^{-1}$ |
| —OH | 3.2 | 3 |
| NH$_2$ | 3 | |
| —CH$_3$ | 3 | 0.7 |
| —OCOCH$_3$ | 0.7 | |
| —NH$_3^+$ | 0.3 | |
| —H | 0.25 | <0.3 |
| —COCH$_3$ | 0.22 | |
| —OSO$_3$ | 0.17 | |
| —CN | 0.07 | |
| —CO$_2$H | 0.03 | 0.005 |

Consistent with the expected electrophilic character of these radicals, the rates decrease with increasing electron-withdrawing power of X. Thus, methanol is about 5 times more reactive than methyl acetate and about 20 times more reactive than methyl sulfate towards hydroxyl radical (HO•). Cu(II) readily oxidizes organic radicals, including methyl and other alkyl radicals, via an organocopper(III) intermediate, L$_n$Cu$^{iii}$ R (Kochi, J. K., A. Bemis and C. L. Jenkins. 1968. "Mechanism of Electron Transfer Oxidation of Alkyl Radicals by Copper(II) Complexes." J. Am. Chem. Soc. 90(17), 4616–4625. Walling, C. 1975. "Fenton's Reagent Revisited." Acc. Chem. Res. 8, 125.). Reductive elimination produces Cu(I) and RL or olefin, depending on the type of alkyl group and ligand. In this capacity, Cu(II) plays a key role in catalyzing organic redox chain reactions involving Fenton's reagent, peroxydisulfate (S$_2$O$_8^{2-}$), and oxygen.

Periana et al. in U.S. Pat. No. 5,233,113 discuss a catalytic process for converting lower alkanes into their corresponding esters using catalytic amounts of Group VIII noble metal. A disadvantage is the cost of the noble metal catalyst.

Further, Periana et al. in U.S. Pat. No. 5,306,855 describe a process for converting lower alkanes to esters, alcohols and hydrocarbons with either noble metal catalyst or mercury or thallium. Disadvantages of this process include the cost of the noble metal catalyst or mercury or thallium, or the toxicity of mercury or thallium. Further disadvantages include the need for regeneration of the acid reagent in stoichiometric amounts for processes having acid reagents.

Hence, there is still a need for a method of converting C—H bond compounds without noble or toxic metals and without the need to electrochemically regenerate a metal ion.

SUMMARY OF THE INVENTION

The present invention is the conversion of a C—H compound in the presence of an acid that may also act as an oxidant or C—H compound in the presence of an acid and a separate oxidant by exposure of an added semiconductor material to light.

It is an object of the present invention to provide a method of selectively converting C—H compounds to esters, olefins, alkenes, alkynes, and combinations thereof.

It is another object of the present invention to provide a method of converting lower, hydrocarbons to higher hydrocarbons.

The subject matter of the present invention is particularly pointed out and distinctly claimed in the concluding portion of this specification. However, both the organization and method of operation, together with further advantages and objects thereof, may best be understood by reference to the following description.

DESCRIPTION OF THE PREFERRED EMBODIMENT(s)

The present invention is the addition of a semiconductor material to a premixture of a C—H compound and an acid, thereby forming a reactive mixture for converting the C—H compound. Upon exposure to light, the C—H compound forms a C—H compound radical. It is necessary to ensure the presence of an oxidant that will oxidize or scavenge electrons from the semiconductor material. In the circumstance that the semiconductor is doped with a precious metal, protons from the acid itself serve as the oxidant. If more oxidant is needed, or if the semiconductor is not doped with a precious metal, at least one other oxidant is added. Oxidants further include oxygen especially in a compound having two oxygen atoms bonded to one another, transition metal ion, compounds containing transition metal ions, conductive electrode, or a combination thereof. An oxidant may be present in the acid or C—H compound prior to forming the premixture. Compounds containing transition metal ions include but are not limited to "ate" compounds for example permanganate, chromates, and non-oxygen oxidants, for example ferricenium. The oxidant(s) is/are further used wherein at least one C—H bond of the C—H compound radical is oxidized to a C—O bond. Depending upon the type or amount of oxidant present, the C—H bond may be converted to a carbon to carbon bond having single, double, or triple bond. In the presence of the acid, a portion of the C=C become converted to a C—O bond. If a separation process is employed, C=C compounds may be extracted from the C—O bond compounds. In the absence of any separation, the conversion will proceed toward C—O bond compounds. As an example, if the starting organic C—H bond material is cyclohexane, and the acid is trifluoroacetic acid, the C=C bond compound is an olefin and the C—O bond compound is an ester.

According to the present invention, radical-based oxidations by an attacking radical that is electrophilic are made selective for alcohols. The attack is normally exothermic and a product organic radical becomes functionalized with an electron-withdrawing group, such that the alpha C—H bond is less electron-rich compared with the C—H bond in the parent compound. A separate subsequent chemical process converts the functionalized compound to an alcohol.

In a preferred embodiment, a premixture containing a C—H compound, acid, and an oxidant is prepared. The premixture may also contain a transition metal ion, but is not required. The C—H compound may be an alkyl for example methane, butane, propane, or cyclohexane. The acid is an acid solution, for example a fully fluorine substituted carboxylic acid (e.g. trifluoroacetic acid), sulfuric acid, trifluoromethane sulfonic acid, halogenated carboxylic acid, or mixtures thereof. The acid solution may be mixed with water or other solvent(s). Where additional oxidant beyond the acid is needed, the additional oxidant is preferably oxygen in the form of a compound containing two oxygen atoms bonded together, for example molecular oxygen gas, peroxide(s), or a combination thereof. Alternatively, the oxidant may be conductive electrodes with an electrical potential. The transition metal ion is selected from the group of Mendeleev Transition Metals, preferred metals being for example Cu(I), Cu(II), V(II), Ti(III), Fe(II), Cr(II), U(IV), or any combination thereof.

To the premixture is added a semiconductor catalyst to form a reactive mixture. The semiconductor is any semiconductor capable of converting energy to oxidants and/or reductants. Preferred semiconductors include but are not limited to titanium dioxide ($TiO_2$), $SrTi_3$, $WO_3$, $ZnO$, doped derivatives of the aforementioned semiconductors and combinations thereof. The amount of catalyst or semiconductor used depends on reactor geometry and method of application. To be effective, the light must be transmitted through the premixture and be absorbed by the semiconductor. Further, the light may be used alone or in combination with electrical energy. Sufficient catalyst is used to absorb all or substantially all of the light of wavelength sufficient to activate the catalyst. It is important that the mixture remains mixable, pumpable, and pourable. The light may be single band, monochromatic, broadband or a combination thereof. Preferably, the light is ultraviolet light. More preferably the ultraviolet light is in the range of 300 to 400 nm.

The semiconductor may be in any form, for example a granular or powder form suspended in the premixture, or attached to a substrate. Alternatively, the semiconductor may be in the form of one or more electrodes, either as monolithic semiconductor material or semiconductor material on a substrate, thereby permitting dual purpose operation for providing oxidant or reductant and regenerating the transition metal ion, if present. When light is used as the energy, it is preferred that the semiconductor be in granular or powder form suspended in the premixture to maximize photon capture. When electricity is used as the energy, it is preferred that the semiconductor be in the form of one or more electrodes for maximizing electron transfer.

Energy to the semiconductor may be in the form of electricity and/or light. When the reactive mixture is exposed to light, preferably ultraviolet light, and/or an electrical potential, an ester product is obtained.

In a preferred embodiment of the present invention, the method has the steps of:

combining in a single vessel a reactant organic compound having a C—H bond, with an acid solution having an H⁺ ion and an acid counter ion, the reactant organic compound contacting the acid solution, thereby forming a premixture;

ensuring the presence of an oxidant;

adding a semiconductor to the premixture forming a reactive mixture; and maintaining the reactive mixture at an operating temperature and pressure while exposing the reactive mixture to light and forming a C—H compound radical that further reacts with the acid in the acid solution to form a C—O compound.

Contacting includes dissolving the organic compound in an acid solution and mixing the organic compound in the acid solution whether or not dissolution occurs.

In one embodiment wherein the oxidant is a compound containing two oxygen atoms bonded to one another and wherein the reactive mixture contains a transition metal ion, the "further reaction" involves oxidizing the organic compound to a carbon radical, further oxidizing the carbon radical with the transition metal ion, and bonding the acid counter ion to the C of the oxidized carbon radical replacing the H thereby producing an oxidized (C—O) organic compound, the acid counter ion bonded to the C of the oxidized organic compound rendering said C stable from further oxidation.

Additional details of yield and parameter sensitivities may be found in 08/056,577 herein incorporated by reference. In 08/056,577, the amount of oxidized organic compound is less than or equal to a stoichiometric amount of the transition metal ion, and the transition metal ion is a reactant. In the present invention, the transition metal ion may be regenerated by the semiconductor.

Operating temperatures may range from just above a solution freezing temperature to just below a solution boiling temperature at a given pressure.

The present invention may be illustrated by a specific reaction wherein the organic is methane, the semiconductor is $TiO_2$, the oxidant is $O_2$, the acid is trifluoroacetic acid, and a metal ion [Cu(II)] is used. Thus, hydroxyl radical is generated from reaction of water with holes (H⁺) formed by photoexcitation of $TiO_2$ (Equation 1) or by electrolysis using semiconductor electrodes, or a combination thereof. Subsequent steps involve hydroxyl radical attacking methane to form the methyl radical (Equation 2), and oxidation of methyl radical by Cu(II) to produce methyl trifluoroacetate (Equation 3).

$$h^+(TiO_2)+H_2O \rightarrow HO\cdot + H^+ \quad (1)$$

$$HO\cdot + CH_4 \rightarrow H_3C\cdot + H_2O \quad (2)$$

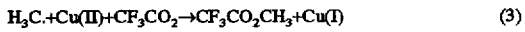
$$H_3C\cdot + Cu(II) + CF_3CO_2 \rightarrow CF_3CO_2CH_3 + Cu(I) \quad (3)$$

Reaction of $O_2$ with Cu(I), formed in Equation 3 and also by reaction of electrons (e) formed by photoexcitation of $TiO_2$ (Equation 4), also forms HO. (Equation 5).

$$e(TiO_2) + Cu(II) \rightarrow Cu(I) \quad (4)$$

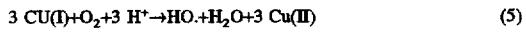
$$3\ Cu(I) + O_2 + 3\ H^+ \rightarrow HO\cdot + H_2O + 3\ Cu(II) \quad (5)$$

Combined with the hydrolysis of methyl trifluoroacetate (Equation 6), the net reaction is equation 7.

$$CF_3CO_2CH_3 + H_2O \rightarrow CH_3OH + CF_3CO_2H \quad (6)$$

$$CH_4 + \tfrac{1}{2}O_2 \rightarrow CH_3OH \quad (7)$$

The energy added may be light, or light and electricity through electrodes. The operation of the selective oxidation of organics through photocatalysis may be enhanced by inserting the semiconductor into the premixture in the form of electrodes and imposing an electrical potential across them.

Adding light reduces the amount of electricity and possibly reduces the electrical voltage needed.

EXAMPLE 1

This experiment demonstrates the present invention by comparing two identical sample mixtures wherein one sample mixture has a catalyst and the other does not.

A reactive mixture was prepared according to the present invention. A first solution of 25-ml trifluoroacetic acid containing between 0.02 to 0.1M $Cu^{+2}$ and ammonium ions in 10 vol % water was prepared in a 50 ml round bottom flask with magnetic stirrer. The round bottom flask was borosilicate glass that absorbs ultraviolet light below about 300 nm. The ammonium ions did not participate or contribute to the reaction. Excess cyclohexane and approximately 0.2 g of photocatalyst HEI 21117-PDO1 ($TiO_2$ immobilized on silica microspheres, supplied by E. Heller & Co., Alameda, Calif.) were then added. The cyclohexane formed a separate liquid phase on top of the trifluoroacetic acid solution.

A second solution (0.02M $Cu^{+2}$ in 10 vol % water/trifluoroacetic acid and 1.5 ml cyclohexane) analogous to the above solution was prepared as a control. No $TiO_2$ catalyst was added to it.

The first and second solutions were separately stirred and irradiated intermittently with a 150-watt long-wave UV lamp (BLAK-RAY B-100 A) over a period of 2 weeks with the first solution containing catalyst receiving approximately 38 hrs of irradiation and the second control solution receiving 22 hrs. Samples were periodically removed and analyzed for products. At the end of the experiments, 1-ml samples were removed from top and bottom layers of first and second solutions and the samples diluted with 10-ml volumes of dichloromethane. A 10-µl quantity of toluene was added to each sample as an internal standard. The samples were then neutralized by shaking with 5-ml portions of saturated sodium bicarbonate. The dichloromethane layers were then separated, dried and analyzed by gas chromatography and gas chromatography-mass spectrometry (GC-MS).

The samples derived from both the top and bottom layers of the first solution samples Containing $TiO_2$ were found to contain a compound that exactly matched the GC-MS spectra and retention time of an authentic sample of cyclohexyl trifluoroacetate. The amount of product (cyclohexane and trifluoroacetic acid layers) was estimated to be approximately 0.5 mmol. The second control solution samples showed the product to be present at not more than 0.025 mmol or 1/20th of this amount produced with catalyst present. No other significant products were detected in either the first solution samples or the second control solution samples.

EXAMPLE 2

A solution of 25 mL of trifluoroacetic acid containing 0.110M $Cu(OH)_2$ and 10 volume % water was placed in a 50-mL round-bottom flask of borosilcate glass that absorbs ultraviolet light below about 300 nm. Approximately 0.2 g of Degussa P25 anatase titanium dioxide (different catalyst compared to Example 1) was added into the trifluoroacetic acid solution. 4-mL cyclohexane was added to the flask. The cyclohexane formed a separate liquid phase on top of the trifluoroacetic acid solution. The solution was irradiated with a 450 watt, long-wave, quartz, mercury-vapor photochemical (medium pressure) immersion lamp (Ace Glass, Canrad-Hanovia model 7825) for 48.5 hours. During irradiation, the solution was stirred vigorously.

After irradiation was complete, 100 μL samples of the cyclohexane and trifluoroacetic acid layers were taken. A 5 μL quantity of toluene was added to each sample and then diluted with approximately 2 mL of gas chromatographic-grade methylene chloride. Solid sodium bicarbonate was added to each sample for neutralization. The diluted and neutralized samples were washed with water and dried over magnesium sulfate.

The dried samples were then analyzed by GC-MS. Both samples showed a product that exactly matched both the retention time and GC-MS spectra of an authentic sample of the ester cyclohexyl trifluoroacetate. The total amount of cyclohexyl trifluoroacetate was found to be 2.08 moles. Although the reaction mixture had turned yellow-brown, no other products were produced in comparable amounts. The amount of cyclohexanone was about 2% of the ester which demonstrates a high selectivity toward the ester, giving a C—O bond to C=O bond ratio by molecular weight of about 50:1. Higher molecular weight products which could be diesters were also detected at low levels similar to cyclohexanone.

EXAMPLE 3

A second solution was prepared as in Example 2 except that no copper ions were added. The second solution was exposed to the lamp, processed, and analyzed in the same manner as the solution in Example 2.

This second solution showed 0.26 moles of cyclohexyl trifluoroacetate after 48.5 hours, which is ⅛ the amount produced in the presence of copper ions. Another product having a mass spectrum and GC retention time matching those consistent with that expected for bicyclohexyl was observed in comparable amounts, which was unexpected. Two other products that were soluble were detected in amounts about a factor of 10 lower, but not identified. No polymers were formed.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method for converting a C—H compound to an ester, said ester stable from further oxidation, comprising the steps of preparing a premixture of said C—H compound with an acid, ensuring that an oxidant is present, oxidizing said C—H compound to form a C—H compound radical, reacting the C—H compound radical with the acid and bonding the acid to the C of the C—H compound and replacing the H and producing the ester, the acid rendering the C stable from further oxidation, wherein the improvement comprises the steps of:

(a) adding a semiconductor to the premixture and forming a reactive mixture; and (b) exposing the reactive mixture to light and forming said C—H compound radical.

2. The method as recited in claim 1, wherein said oxidant is selected from the group consisting of proton, transition metal ion, a compound containing two oxygen atoms bonded to one another, electrical potential, and combinations thereof.

3. The method as recited in claim 2, wherein said semiconductor is doped with a precious metal and the oxidant is the proton from the acid.

4. The method as recited in claim 3, wherein said reacting the C—H compound radical is with said oxidant.

5. The method as recited in claim 4, wherein said oxidant is said transition metal ion.

6. The method as recited in claim 5, wherein said transition metal ion is a copper ion.

7. The method as recited in claim 3, wherein said electrical potential is applied through an electrically conductive electrode.

8. The method as recited in claim 1, wherein said reacting is disproportionation.

9. The method as recited in claim 8, wherein said disproportionation is followed by acid esterification.

10. The method as recited in claim 8, wherein said disproportionation is followed by a separation.

11. The method as recited in claim 1, wherein said semiconductor is a powder.

12. The method as recited in claim 1, wherein said semiconductor is in the form of an electrode or a pair of electrodes.

13. The method as recited in claim 1, wherein said light is ultraviolet light.

14. The method as recited in claim 13, wherein said ultraviolet light is in the range of 300 to 400 nm.

15. The method as recited in claim 1, wherein said C—H compound is a hydrocarbon.

16. The method as recited in claim 15, wherein said hydrocarbon is an alkane.

17. The method as recited in claim 1, wherein said C—H compound radical forms a second compound wherein the C—H bond of said C—H compound radical is converted to a carbon to carbon bond selected from the group consisting of C—C bond, C=C bond, C≡C bond and combinations thereof.

18. The method as recited in claim 17, further comprising separating said second compound from said ester.

19. A method of converting a C—H compound to an ester, comprising the steps of:

(a) combining in a single vessel a reactant organic compound having a C—H bond, with an acid solution having an $H^+$ ion and an acid counter ion, the reactant organic compound contacting the acid solution, and forming a premixture;

(b) ensuring that an oxidant is present;

(c) adding a semiconductor to the premixture forming a reactive mixture; and (d) maintaining the reactive mixture at an operating temperature and pressure while exposing the reactive mixture to light and forming a C—H compound radical and reacting with the acid counter ion and the oxidant in the acid solution and bonding the acid to the C of the C—H compound and replacing the H and producing the ester, the acid counter ion rendering the C stable from further oxidation.

20. The method as recited in claim 19, wherein the oxidant is selected from the group consisting of proton, transition metal ion, a compound containing two oxygen atoms bonded to one another, electrical potential, and combinations thereof.

21. The method as recited in claim 19, further comprising adding a transition metal ion in the premixture.

22. The method as recited in claim 21, wherein the reacting is oxidizing the transition metal ion to a higher valence state.

* * * * *